(12) United States Patent
Stangl et al.

(10) Patent No.: US 9,885,597 B2
(45) Date of Patent: Feb. 6, 2018

(54) LIQUID TANK WITH AN ULTRASONIC SENSOR

(71) Applicant: Continental Automotive GmbH, Hannover (DE)

(72) Inventors: Ronny Stangl, Thalmassing (DE); Stephan Heinrich, Pfeffenhausen (DE); Denny Schaedlich, Neustadt (DE)

(73) Assignee: CONTINENTAL AUTOMOTIVE GMBH, Hanover (DE)

( * ) Notice: Subject to any disclaimer, the term of this patent is extended or adjusted under 35 U.S.C. 154(b) by 19 days.

(21) Appl. No.: 15/025,432

(22) PCT Filed: Sep. 23, 2014

(86) PCT No.: PCT/EP2014/070163
§ 371 (c)(1),
(2) Date: Mar. 28, 2016

(87) PCT Pub. No.: WO2015/044096
PCT Pub. Date: Apr. 2, 2015

(65) Prior Publication Data
US 2016/0216148 A1    Jul. 28, 2016

(30) Foreign Application Priority Data
Sep. 27, 2013    (DE) .................. 10 2013 219 643

(51) Int. Cl.
*G01F 23/296*    (2006.01)
*G01N 29/22*    (2006.01)

(52) U.S. Cl.
CPC ....... *G01F 23/2962* (2013.01); *G01N 29/221* (2013.01); *G01N 29/223* (2013.01)

(58) Field of Classification Search
CPC . G01F 23/2962; G01N 29/221; G01N 29/223
See application file for complete search history.

(56) References Cited

U.S. PATENT DOCUMENTS

| 5,471,872 A | 12/1995 | Cummings ................ 73/290 V |
| 6,360,599 B1 | 3/2002 | Pathak et al. ............. 73/290 V |

(Continued)

FOREIGN PATENT DOCUMENTS

| DE | 1548930 A1 | 7/1969 | ........... G01F 23/296 |
| DE | 102006017284 A1 | 10/2007 | ........... G01F 23/296 |

(Continued)

OTHER PUBLICATIONS

Japanese Office Action, Application No. 2016517352, 3 pages, Mar. 13, 2017.

(Continued)

Primary Examiner — Lisa Caputo
Assistant Examiner — Punam Roy
(74) Attorney, Agent, or Firm — Slayden Grubert Beard PLLC

(57) ABSTRACT

The present disclosure describes a tank comprising an ultrasonic sensor, a first cylindrical reflector, and a second cylindrical reflector. The ultrasonic sensor may be disposed on the floor of the tank for measuring the signal propagation time through a liquid located in the tank and comprise a transmitter/receiver.

18 Claims, 1 Drawing Sheet

(56) References Cited

U.S. PATENT DOCUMENTS

| | | | | |
|---|---|---|---|---|
| 7,966,882 B2 * | 6/2011 | Greenwood | ......... | G01N 29/024 |
| | | | | 73/30.01 |
| 8,037,752 B2 | 10/2011 | Zachmann et al. | ......... | 73/290 V |
| 9,605,990 B2 * | 3/2017 | Enomoto | ............ | G01F 23/2962 |
| 2010/0018309 A1 * | 1/2010 | Marcovecchio | .... | G01F 23/2962 |
| | | | | 73/290 V |
| 2012/0118059 A1 * | 5/2012 | Reimer | ................ | F01N 3/2066 |
| | | | | 73/290 V |

FOREIGN PATENT DOCUMENTS

| | | | | | |
|---|---|---|---|---|---|
| EP | 0167338 | A2 | | 1/1986 | ........... G01F 23/296 |
| EP | 0813044 | A2 | | 12/1997 | ........... G01F 23/296 |
| GB | 1090652 | A | * | 11/1967 | ......... G01F 23/2962 |
| GB | 1123939 | A | | 8/1968 | ............. G01F 23/28 |
| JP | 61247959 | A | | 11/1986 | |
| JP | 2001108507 | A | | 4/2001 | |
| JP | 2001208595 | A | | 8/2001 | |
| JP | 2002022712 | A | | 1/2002 | |
| JP | 2002131298 | A | | 5/2002 | |
| JP | 2004317125 | A | | 11/2004 | |
| WO | 2009/074428 | A1 | | 6/2009 | ........... G01F 23/296 |
| WO | WO 2014027561 | A1 | * | 2/2014 | ........... G01F 23/296 |
| WO | 2015/044096 | A1 | | 4/2015 | ........... G01F 23/296 |

OTHER PUBLICATIONS

German Office Action, Application No. 102013219643.1, 5 pages, dated Jul. 2, 2014.
International Search Report and Written Opinion, Application No. PCT/EP2014/070163, 14 pages, dated Dec. 3, 2014.

* cited by examiner

LIQUID TANK WITH AN ULTRASONIC SENSOR

CROSS-REFERENCE TO RELATED APPLICATIONS

This application is a U.S. National Stage Application of International Application No. PCT/EP2014/070163 filed Sep. 23, 2014, which designates the United States of America, and claims priority to DE Application No. 10 2013 219 643.1 filed Sep. 27, 2013, the contents of which are hereby incorporated by reference in their entirety

TECHNICAL FIELD

The present disclosure relates to a sensor for a liquid tank and more particularly to an ultrasonic sensor for a liquid tank.

BACKGROUND

During the measurement of propagation time by means of ultrasonic sound, an ultrasonic wave is emitted by a transmitter, passes through an indeterminate distance and subsequently impinges on the receiver. If the propagation speed and the distance from an object are known, the propagation time of the wave can be determined. Since the transmitter (e.g., an ultrasonic transducer) is a transmitter-receiver combination, the emitted sound wave must be reflected in order to be able to be sensed again. Reflectors arranged in the sound path are used for this.

If the measurement system is composed of different materials, however, multiple problems arise. As a result of different coefficients of thermal expansion of the materials, the expansion due to a changing temperature is unequal at multiple points. This brings about a change in the measurement distance and therefore falsifies the reference distance. If, for example, a reflector made of stainless steel is attached to a plastic housing, when there is a change in the temperature the distance between the transmitter-receiver combination and the reflector will change. Furthermore, satisfactory functionality of the system cannot be ensured as a result of aging of the components. If expansion, rotation, stresses, or other wear of the individual components occur at individual points over the service life of the mechanical structure, adverse effects on the measuring unit may result. In order to limit these effects, a measurement is carried out with two reflectors (or references). In this context it is to be noted that the two reflector faces or reference faces are composed of the same material or same permanently connected parts in order to limit the mentioned effects such as heat, expansion, or aging to a single material. The propagation time of the distance between the transmitter-reflector-receiver is no longer measured here but instead the difference in propagation time between the two reflector faces (reference faces) which are different distances away.

A known ultrasonic sensor is located in a closed container (tank) which is filled with liquid. The object of the sensor is to determine the concentration of the liquid by means of a propagation time measurement. Furthermore, the sensor may measure the current filling level. In this context, the mechanical structure is arranged in such a way that a part of the sound wave which is output by a transmitter/receiver is reflected at a reference structure with two reflectors. Another part of the wave is directed to the surface of the liquid via a mirror, in order to determine the filling level.

The reference structure is arranged here in a horizontal (planar) fashion, wherein the two reflectors are formed by planar faces of the common reference structure which are at a different distance from the transmitter/receiver. This horizontal reference structure has the advantage that it is not located directly in the sound path, with the result that an excessively large part of the signal is not screened and therefore a filling level measurement is possible.

Since the overall height of the reference structure of such an ultrasonic sensor is relatively small, the risk of the accumulation of dirt which can lead to measurement falsifications is very large. Fabrication tolerances of the ultrasonic transducers can give rise to different emission angles of the sound beams and also act to a relatively pronounced degree on the measuring accuracy in the case of relatively flat reference structures which are embodied in such a way. Finally, with such reference structures with planar reference faces there is the following problem: when the container is refueled, air bubbles are also swept in or come about and become lodged at various components, which can cause a measurement to be falsified or entirely prevented. In the case of a rising temperature, gas bubbles can also form in the system as a result of out gassing if it has not yet happened as a result of the refueling process. Such bubbles can impede the measurement system, in particular can cause multiple reflections or undesired signal deflections which can falsify the measurement result.

A liquid tank is known from DE 15 48 930 A. In this publication, an ultrasonic device for measuring the level of a liquid is described. The ultrasonic wave path runs perpendicularly with respect to the level of the liquid here, and the reflectors are arranged in the form of horizontal cylinders.

U.S. Pat. No. 6,360,599 B1 discloses a device and a method for measuring a liquid level. In this device, the ultrasonic sound path also runs perpendicularly with respect to the level of the liquid, and cylindrical reflectors which are arranged in a horizontal fashion are provided.

DE 10 2006 017 284 A1 relates to a device for measuring the filling level of a liquid in a pipe with an ultrasonic sensor which is arranged on the floor of a liquid tank. A planar reflector is used here.

The device which is described in WO 2009/074428 A1 and which has the purpose of measuring a filling level of a liquid in a container has an ultrasonic sensor which is arranged on the floor of the container and has corresponding sound-conducting bodies which are embodied in a tube shape.

SUMMARY OF THE INVENTION

The present disclosure provides a liquid tank with an ultrasonic sensor distinguished by a particularly high measuring accuracy accompanied by the possibility of simple fabrication.

The term "cylinder" is understood to mean here such a basic surface which is embodied as desired if at least part of its lateral surface on which the signals impinge is embodied in a curved fashion. Circular cylinders and standing cylinders (with an axis which runs perpendicular to the base surface) may be used.

Flat planar reflectors may provide a high intensity of the reflected signal. In some embodiments, a signal with low signal intensity is accepted owing to the cylinders which are used, in particular circular cylinders, since a series of other advantages can be achieved with such reflectors in the form of a cylinder. The sensor is relatively insensitive to soiling which accumulates on the floor of a tank, etc., since the reflectors are not embodied as horizontal structures but rather in the form of standing cylinders which have a relatively high overall height. A certain degree of insensitivity to fabrication variations of the transmitter (sound beam) is also achieved. In addition, the round surface of the cylinders impedes the adhesion of bubbles, since there is no level face present.

Embodiments of the sensor according to the present disclosure are relatively insensitive to mechanical tolerances which are caused by rotation or positional tolerances of the reflectors. In particular, if the reflectors are in the form of a circular cylinder, only a small angle dependence or no angle dependence at all is present compared to planar references, since, as a result of the rotational symmetry of a circular cylinder, the geometric reflection range is identical from each angle at which the radiation strikes.

The diameter of the reflection cylinders plays only a subordinate role in terms of the reflective range. If a small diameter is used, but at the same time with a certain component height, the cylinder can be positioned very close to the region of the main beam of the emitted sound wave without excessively covering the latter. Since the overall height of the reflection cylinder can be selected freely, particle deposits on the foot of the reflector are, as mentioned, not troublesome, with the result that the entire system is therefore insensitive to soiling.

As a result of the freely selectable overall height, the adverse effect of the deviation of the emission angle of the sound beam which is caused by fabrication variations of the transducer is also reduced. If the sound wave is not emitted horizontally, the size of the face lying in the sound cone becomes smaller given a conventional lying reference structure, which brings about weakening of the received sound wave. This effect is significantly neutralized with the described design of the reflectors as bar reflectors.

In addition, the fabrication of a reference structure as a planar reflector is technically more complex, since the parts are subject to certain rules in terms of orientation and tolerance. At present, they are milled, punched or bent. When line reflectors are used, as is the case with the circular cylinder used here, the technical complexity is decreased, since round materials of any diameter are available in a finished form as bar material. As a result of the relatively high degree of independence in the case of the diameter, there are no particular problems with tolerances here either.

In some embodiments, the two reflectors are arranged on a common plate which is composed of the same material as the reflectors. As a result, in particular problems with different coefficients of thermal expansion are avoided. The ultrasonic sensor can, in addition, have a mirror which is arranged in the ultrasonic path behind the two reflectors and has the purpose of deflecting sound. As already mentioned, the two reflectors preferably have a relatively small diameter, with the result that they do not significantly impede the propagation of sound to the mirror which is used for deflecting sound.

The ultrasonic sensor may measure the concentration of a liquid. It can additionally measure the filling level of the liquid, for which purpose the corresponding deflection of sound with a mirror is used. The sensor is arranged on the floor of a liquid tank and preferably serves here to measure the concentration of the liquid located in the tank by means of a propagation time measurement which is carried out. In addition, the liquid level in the tank can be measured by means of a corresponding propagation time measurement.

Specifically, the ultrasonic sensor according to the teachings of the present disclosure can be used to measure the concentration of a urea solution in a tank. Such tanks are located in motor vehicles and serve to carry a urea solution which is fed into the exhaust gas of the motor vehicle in order to reduce the $NO_x$ concentration therein.

BRIEF DESCRIPTION OF THE DRAWINGS

The invention will be explained in detail below by means of an exemplary embodiment and in conjunction with the drawing, in which.

DETAILED DESCRIPTION

Figure 1:
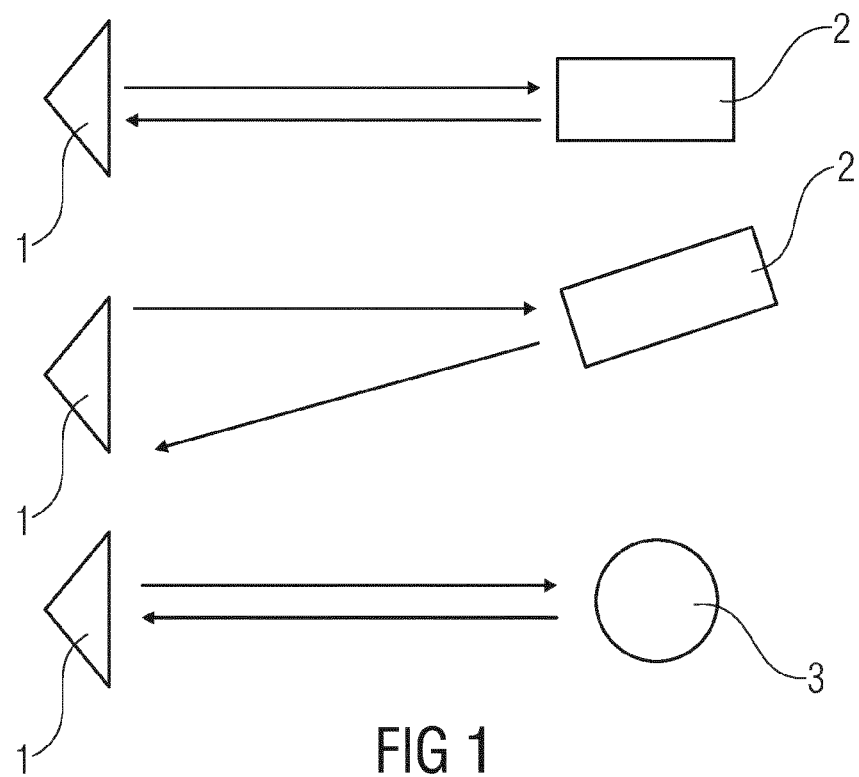
FIG. 1 is a schematic illustration of a transmitter/receiver and of a reflector, wherein the reflector is provided, on the one hand, with a planar reflection face and, on the other hand, with a round reflection face.

FIG. 1 shows, in the upper diagram, a schematic view of a transmitter/receiver 1 and a reflector 2 which has a planar reflection face. In the illustration of the upper figure, the reflector 2 assumes its precise position, with the result that the reflected beam runs parallel to the incident beam. Precise measurement of the ultrasonic propagation time is possible with this arrangement.

In the illustration of the middle diagram, the reflector 2 is rotated with respect to the position of the upper illustration. The reflected beam is therefore deflected and no longer impinges directly on the receiver, which entails severe screening of the signal. This effect does not occur with a bar reflector 3 which is present in the lower diagram in FIG. 1. With such a bar reflector 3 in the form of a standing cylinder there is no such angular dependence, since, as a result of the rotational symmetry of a cylinder, the geometric reflection range is identical from each angle at which the radiation strikes. Such a bar reflector in the form of a standing circular cylinder is used in the ultrasonic sensor embodied according to the invention.

Figure 2:
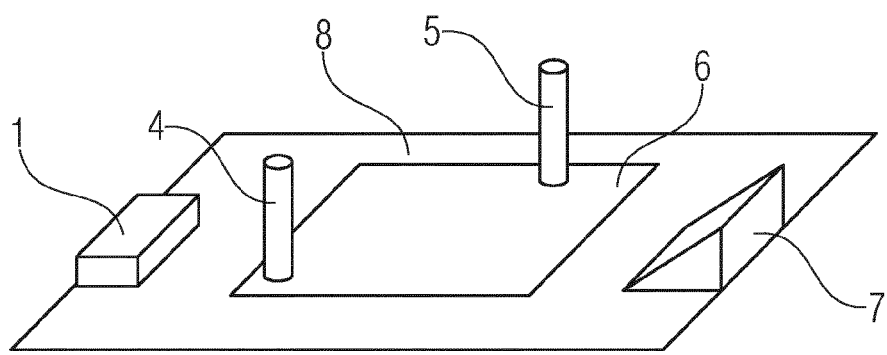
FIG. 2 shows the schematic design of an ultrasonic sensor which has two reflectors in the form of standing cylinders.

FIG. 2 is a schematic view of the design of an ultrasonic sensor which is arranged on the floor 8 of a liquid tank, for example of a tank which accommodates a urea solution. A transmitter/receiver 1 outputs ultrasonic waves in the form of a sound beam (not shown), the central axis of which runs approximately horizontally. The ultrasonic waves propagate through the liquid present in the tank and impinge here on a reference structure which has two reflectors 4, 5, which are each in the form of a standing circular cylinder. The two reflectors 4, 5 are attached to a common plate 6. The reflectors 4, 5 and the plate 6 are composed of the same material.

The reflectors 4, 5 are arranged in the ultrasonic wave path in such a way that although they are positioned very close to the region of the main beam of the emitted sound wave, they do not cover it excessively. The reflectors 4, 5 which are formed as standing cylinders are relatively insensitive to rotation or position tolerances, to soiling (depositing of particles near to the ground) and with respect to fabrication variations of the transmitter/receiver. They impede the adhesion of bubbles and are easy to fabricate.

The sound waves which are emitted by the transmitter/receiver 1 impinge linearly on the two reflectors 4, 5. The reflected waves are received by the transmitter/receiver 1. The concentration of the liquid located in the tank can be determined from the measured propagation time.

The sound waves which are emitted by the transmitter/receiver 1 also impinge on the mirror 7 and are deflected upward from there. They impinge on the surface of the liquid and are reflected back from there to the transmitter/receiver via the mirror 7. The liquid level can be determined from the measured propagation time.

What is claimed is:

1. A tank comprising:
   an ultrasonic sensor disposed on the floor of the tank for measuring the propagation time in a liquid located in the tank, comprising a transmitter/receiver emitting sound waves across the floor of the tank, and
   a first cylindrical reflector and a second cylindrical reflector extending from the floor of the tank and offset from a main path of the emitted sound waves to reflect a portion of the emitted sound waves back to the ultrasonic sensor.

2. The tank as claimed in claim 1, wherein the two reflectors are arranged on a common plate composed of the same material as the reflectors.

3. The tank as claimed in claim 1, further comprising a mirror arranged in the ultrasonic wave path behind the two reflectors for deflecting sound.

4. The tank as claimed in claim 1, wherein the ultrasonic sensor detects a propagation time of the emitted sound waves reflected from the first cylindrical reflector and the second cylindrical reflector, wherein the propagation time is associated with a concentration of the liquid in the tank.

5. The tank as claimed in claim 1, further comprising a mirror arranged in the main path of the emitted sound waves to deflect at least a portion of the sound waves toward a surface of the liquid and to return sound waves reflected from the surface of the liquid back to the ultrasonic sensor to measure a propagation time associated with a filling level of the liquid.

6. The tank as claimed in claim 1, wherein the liquid comprises a urea solution.

7. A sensor for measuring a characteristic of a liquid held in a tank, the sensor comprising:
   an ultrasonic transmitter/receiver disposed on a floor of the tank, the ultrasonic transmitter/receiver emitting sound waves across the floor of the tank, and
   a first cylindrical reflector and a second cylindrical reflector extending from the floor of the tank and offset from a main path of the emitted sound waves to reflect a portion of the emitted sound waves back to the ultrasonic transmitter, and
   wherein the ultrasonic receiver measures the propagation time of the signal through the liquid located in the tank.

8. The sensor as claimed in claim 7, wherein the two cylindrical reflectors are arranged on a common plate composed of the same material as the reflectors.

9. The sensor as claimed in claim 7, further comprising a mirror arranged in a path of the ultrasonic signal behind the two reflectors for deflecting sound.

10. The sensor as claimed in claim 7, wherein the ultrasonic sensor detects a propagation time of the emitted sound waves reflected from the first cylindrical reflector and the second cylindrical reflector, wherein the propagation time is associated with a concentration of the liquid in the tank.

11. The sensor as claimed in claim 7, further comprising a mirror arranged in the main path of the emitted sound waves to deflect at least a portion of the sound waves toward a surface of the liquid and to return sound waves reflected from the surface of the liquid back to the ultrasonic sensor to measure a propagation time associated with a filling level of the liquid.

12. The sensor as claimed in claim 7, wherein the liquid comprises a urea solution.

13. A tank for a liquid fed into the exhaust gas of the motor vehicle in order to reduce the NOx concentration therein, the tank comprising:
   a vessel for holding the liquid, the vessel having a floor defined by the side closest to ground,
   an ultrasonic transmitter disposed on the floor of the tank emitting a signal into the liquid, the signal comprising sound waves propagating along a main path across the floor of the tank,
   a first cylindrical reflector and a second cylindrical reflector extending from the floor of the tank and offset from the main path of the emitted sound waves to reflect a portion of the emitted sound waves back to the ultrasonic sensor, and
   an ultrasonic receiver recording a time required for the signal to propagate through the liquid located in the tank.

14. The tank as claimed in claim 13, wherein the two cylindrical reflectors are arranged on a common plate composed of the same material as the reflectors.

15. The tank as claimed in claim 13, further comprising a mirror arranged in a path of the ultrasonic signal behind the two reflectors for deflecting sound.

16. The tank as claimed in claim 13, wherein the time required for the signal to propagate through the liquid located in the tank associated with a concentration of the liquid in the tank.

17. The tank as claimed in claim 13, further comprising a mirror arranged in the main path of the emitted sound waves to deflect at least a portion of the sound waves toward a surface of the liquid and to return sound waves reflected from the surface of the liquid back to the ultrasonic receiver, wherein the time required for the signal to propagate through the liquid located in the tank is associated with a filling level of the liquid.

18. The tank as claimed in claim 13, wherein the liquid comprises a urea solution.

\* \* \* \* \*